United States Patent
Gunn et al.

(10) Patent No.: US 9,504,606 B2
(45) Date of Patent: Nov. 29, 2016

(54) SYSTEMS AND METHODS FOR AN ELECTROCAPILLARY POSITIVE DISPLACEMENT PUMP FOR AN INTRAOCULAR IMPLANT

(71) Applicant: NOVARTIS AG, Basel (CH)

(72) Inventors: Nicholas M. Gunn, Newport Beach, CA (US); Andrew D. Johnson, Tustin, CA (US)

(73) Assignee: Novartis AG, Basel (CH)

( * ) Notice: Subject to any disclaimer, the term of this patent is extended or adjusted under 35 U.S.C. 154(b) by 221 days.

(21) Appl. No.: 14/181,824

(22) Filed: Feb. 17, 2014

(65) Prior Publication Data
US 2015/0230982 A1    Aug. 20, 2015

(51) Int. Cl.
*A61M 5/00* (2006.01)
*A61F 9/007* (2006.01)
*A61M 5/142* (2006.01)

(52) U.S. Cl.
CPC ...... *A61F 9/00781* (2013.01); *A61M 5/14224* (2013.01); *A61M 5/14276* (2013.01); *A61F 2250/0008* (2013.01); *A61F 2250/0013* (2013.01); *A61M 2205/0244* (2013.01); *A61M 2210/0612* (2013.01)

(58) Field of Classification Search
CPC .......... A61F 9/00781; A61F 9/00761; A61F 9/007; A61F 9/0017; A61M 27/002; A61M 2210/0612; F04B 17/00
USPC ....... 604/8–10; 623/4.1, 1.12; 424/422, 423; 417/393
See application file for complete search history.

(56) References Cited

U.S. PATENT DOCUMENTS

| | | | |
|---|---|---|---|
| 6,168,575 B1 | 1/2001 | Soltanpour | |
| 8,891,949 B2 | 11/2014 | Hong et al. | |
| 2002/0114715 A1* | 8/2002 | Yoon | F04B 17/00 417/393 |
| 2005/0049578 A1* | 3/2005 | Tu | A61B 3/16 604/890.1 |
| 2008/0118790 A1 | 5/2008 | Kim et al. | |
| 2008/0280112 A1 | 11/2008 | Langereis et al. | |
| 2009/0240215 A1 | 9/2009 | Humayun et al. | |
| 2012/0148931 A1 | 6/2012 | Kim et al. | |

OTHER PUBLICATIONS

Lee, J. et al, "Liquid Micromotor Driven by Continuous Electrowetting", Proceedings of MEMS'98, 11th IEEE International Workshop Micro Electromechanical System, Heidelberg, Germany, Jan. 25-29, 1998, pp. 538-543.

* cited by examiner

*Primary Examiner* — Philip R Wiest
(74) *Attorney, Agent, or Firm* — Kenneth D. Bassinger

(57) ABSTRACT

A microfluidic pump for implantation proximate an eye of a patient is disclosed herein. The microfluidic pump includes a first substrate with a microfluidic actuator that includes a first chamber and a second chamber coupled by a channel, an electrode in each of the chambers, and a slug positioned within the channel. The slug is displaceable by an electric potential. The microfluidic actuator of the microfluidic pump includes a reservoir aligned with the chamber, a membrane portion separating the reservoir and the chamber, and a second reservoir aligned with the second chamber. A second membrane portion separates the second reservoir and the second chamber. Each of the reservoirs has an inlet and an outlet; each of the inlets has a valve that prevents backflow. A second substrate of the microfluidic pump includes a flow path coupling the outlet of the first reservoir to the inlet of the second reservoir.

18 Claims, 4 Drawing Sheets

SYSTEMS AND METHODS FOR AN ELECTROCAPILLARY POSITIVE DISPLACEMENT PUMP FOR AN INTRAOCULAR IMPLANT

BACKGROUND

The present disclosure relates generally to microfluidic pump systems and methods for ophthalmic treatments. More particularly, the present disclosure relates to microfluidic pump systems that may be used to drain fluid from an eye having a potentially harmful excess thereof.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

FIG. 1 is a diagram of the front portion of an eye 100 that helps to explain the processes of glaucoma. In FIG. 1, representations of the lens 110, cornea 120, iris 130, ciliary body 140, trabecular meshwork 150, Schlemm's canal 160, and the edges of the sclera 170 are pictured. Anatomically, the anterior segment of the eye includes the structures that cause elevated IOP which may lead to glaucoma. Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber 180. The edge of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 generates resistance to the outflow of aqueous humor and provides a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber 180. The sclera 170, the white of the eye, connects to the cornea 120, forming the outer, structural layer of the eye. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

As part of a method for treating glaucoma, a doctor may implant a device in a patient's eye. The device may monitor the pressure in a patient's eye and facilitate control of that pressure by allowing excess aqueous humor to flow from the anterior chamber of the eye to a drainage site, relieving pressure in the eye and thus lowering IOP. Under certain conditions, the drainage site may become obstructed or pressurized. In such circumstances, the obstruction of the drainage site may lead to an undesired cessation of draining and cause the pressure to rise to a potentially harmful pressure within the anterior chamber of the eye.

The system and methods disclosed herein overcome one or more of the deficiencies of the prior art.

SUMMARY

In one exemplary aspect, the present disclosure is directed to a microfluidic pump for implantation proximate an eye of a patient. The microfluidic pump includes a first substrate that has a microfluidic actuator. The microfluidic actuator includes a first chamber and a second chamber coupled by a channel, an electrode in each of the first and second chambers, and a slug positioned within the channel. The slug is displaceable by applying an electric potential to an electrolytic fluid in the first and second chambers and the channel. The microfluidic actuator of the microfluidic pump further includes a first reservoir aligned with the first chamber, a first membrane portion separating the first reservoir and the first chamber, and a second reservoir aligned with the second chamber. A second membrane portion separates the second reservoir and the second chamber. Each of the first and second reservoirs has an inlet and an outlet, and each of the inlets has a valve that prevents backflow through the inlet. A second substrate of the microfluidic pump includes a flow path that couples the outlet of the first reservoir to the inlet of the second reservoir. The first and second substrates of the microfluidic pump are coupled together.

In another exemplary aspect, the present disclosure is directed to a microfluidic pump for implantation proximate an eye of a patient. The microfluidic pump includes a microfluidic actuator that has a first chamber and a second chamber, the first and second chambers being coupled by a channel. The pump further includes a first reservoir aligned with the first chamber of the microfluidic actuator and a first membrane portion separating the first reservoir from the first chamber. The microfluidic actuator is configured to deflect the first membrane portion into and out of the first reservoir. The pump also includes a second reservoir aligned with the second chamber of the microfluidic actuator, with a second membrane portion separating the second reservoir from the second chamber. The microfluidic actuator is configured to deflect the second membrane portion into and out of the second reservoir. Additionally, the microfluidic pump includes a first substrate having a flow path therethrough, the flow path including an inlet channel that couples a pump inlet to an inlet of the first reservoir and to an inlet of the second reservoir. The first substrate is coupled to the microfluidic actuator and the first and second reservoirs.

In yet another exemplary aspects, the present disclosure is directed to an intraocular device for implantation proximate an eye of a patient. The intraocular device includes a plate sized for positioning next to the globe of the eye, a first drainage tube with a proximal end and a distal end, the distal end being configured for insertion into the eye, and a microfluidic pump disposed within the plate and coupled to the proximal end of the first drainage tube. The microfluidic pump includes a microfluidic actuator that has a first chamber and a second chamber. The first and second chambers are coupled by a channel. The microfluidic pump further includes a first reservoir aligned with the first chamber of the microfluidic actuator and a second reservoir aligned with the second chamber of the microfluidic actuator. A first membrane portion separates the first reservoir from the first chamber and a second membrane portion separates the second reservoir from the second chamber. The microfluidic actuator is configured to deflect the first membrane portion into and out of the first reservoir and to deflect the second membrane portion into and out of the second reservoir. The microfluidic pump also includes a first substrate that has a flow path therethrough. The flow path has an inlet channel that couples a pump inlet to an inlet of the first reservoir and to an inlet of the second reservoir. The substrate is coupled to the microfluidic actuator and the first and second reservoirs.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
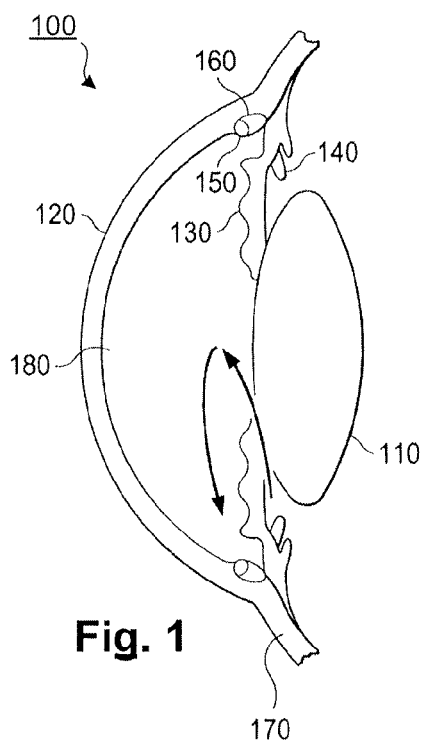
FIG. 1 is a cross-sectional view of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to systems and methods for maintaining a desired intraocular pressure in an eye of a patient by using an intraocular implant device that contains a microfluidic pump. In some aspects described herein, the microfluidic pump includes two or more microfluidic actuators coupled to a flow path that drains fluid from the anterior chamber 180 of the eye 100, even when the pressure within a drainage bleb exceeds the pressure in the anterior chamber or there is added resistance to preventing the desired drainage. The systems and methods disclosed herein may enable better control and maintenance of intraocular pressure, potentially providing more effective treatment and greater customer satisfaction. In some aspects, the intraocular device is an intraocular pressure (IOP) controlling device, such as a glaucoma drainage device (GDD) that alleviates elevated IOP in a patient's eye.

Figure 2:
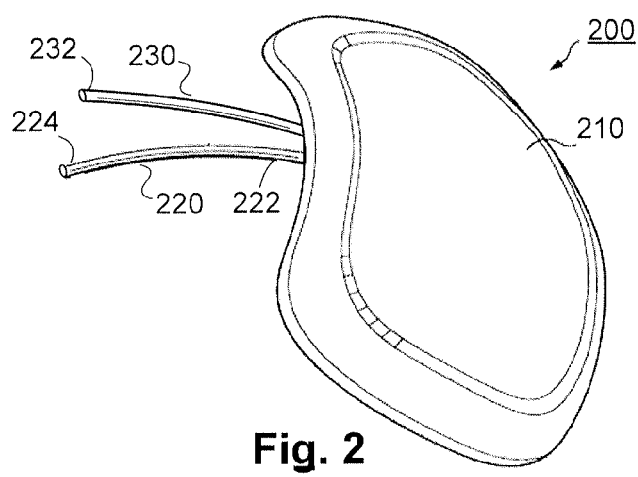
FIG. 2 is a perspective view of an intraocular implant device that carries a microfluidic chamber.

FIG. 2 is a schematic diagram of an intraocular implant or device 200 useable in the monitoring and treatment of a patient's eye. As depicted, the intraocular device 200 is a GDD. The intraocular device 200 includes a body referred to herein as a plate 210 with a first drainage tube 220 that extends from the plate 210. The first drainage tube 220 includes a proximal end portion 222 that couples the tube to one or more structures internal to the plate 210, such a microfluidic pump as will be described herein. A distal end portion 224 of the first drainage tube 220 may be coupled to the eye of a patient to allow for the monitoring of pressure and/or the drainage of fluid. Embodiments of the intraocular device 200 may include additional tubes for priming and/or for the detection of pressure at other location. As illustrated, the intraocular device 200 also includes a second drainage tube 230 that has a distal end 232. The second drainage tube 230 may be connected to the other end of the microfluidic pump. Thus, the first drainage tube 220 and the second drainage tube 230 form part of a microfluidic pump system. An associated pump system will be discussed in greater detail below.

Figure 3:
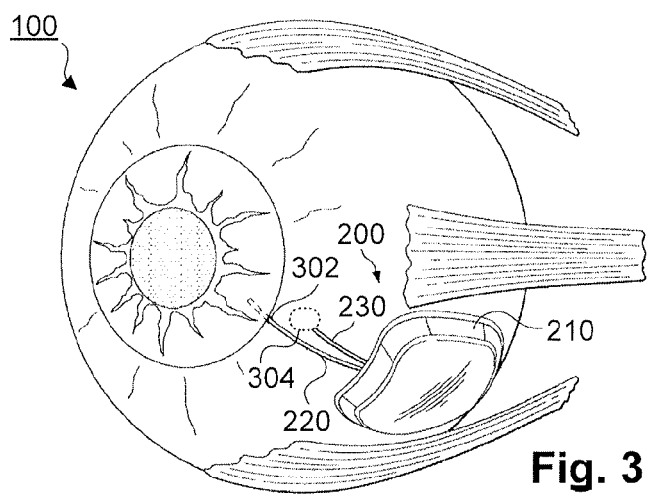
FIG. 3 is a perspective view of an intraocular implant device as situated proximate an eye according to an exemplary aspect of the present disclosure.

FIG. 3 is a schematic diagram of an eye 100 (the anterior portion of which is shown in cross-section in FIG. 1) of a patient whose IOP is being monitored and who is receiving treatment with the intraocular device 200. The intraocular device 200 may be a GDD as depicted in FIG. 2. The plate 210 may include or be arranged to carry various components of an IOP control system, including for example, one or more of a power source, a processor, a memory, a data transmission module, and a flow control mechanism (e.g., a valve system). It may also carry one or more pressure sensor systems, including one or more pressure sensors, to monitor the pressures in and around the eye, including an intraocular pressure. This pressure may be used by other systems within the intraocular device 200, such as drainage systems used to regulate the intraocular pressure.

The plate 210 is configured to fit at least partially within the subconjunctival space and is sized within a range between about 15 mm×12 mm to about 30 mm×15 mm and has a thickness less than about 2 mm thick, preferably less than about 1 mm thick. The plate 210 may be formed to the radius of the eye globe (about 0.5 inches). It may be rigid and preformed with a curvature suitable to substantially conform to the globe or it may be flexible and can flex to conform to the globe. Some embodiments are small enough that conforming to the globe provides little benefit in comfort or implantation technique. The above dimensions are exemplary only, and other sizes and arrangements are contemplated herein.

In some embodiments, the first drainage tube 220 extends from an anterior side of the plate 210 and is sized and arranged to extend into the anterior chamber 180 (as seen in FIG. 1) of the eye through a surgically formed opening 302 in the sclera. The first drainage tube 220 is used to facilitate drainage and may also permit the measure of pressure within the anterior chamber 180. The first drainage tube 220 includes a first open end that may be disposed at a location where pressure measurements may be desired (in this instance within the anterior chamber 180) and from which fluid is drained, and at least one lumen that extends to a second open end that is disposed within or connected to the plate 210. Prior to placement around a patient's eye as depicted in FIG. 3, a chamber within the plate 210 may be primed by the injection of liquid that displaces a gas from the chambers, channels, and/or valves within the device 200. The liquid may be injected through the tube 220 until some liquid may exit through an outlet. In some instances, the outlet is provided by the second drainage tube 230. As illustrated in FIG. 3, the distal end 232 of the second drainage tube 230 is positioned under a bleb 304 formed on the exterior of the sclera 170. The bleb 304 may protect and maintain the distal end 232 of the drainage tube 230 in a desired location to facilitate drainage and/or measure atmospheric pressure experienced by the eye 100. In some embodiments, the fluid entering the device 200 through the first drainage tube 220 may be drained, not through the second drainage tube 230, but through a drain integrated in the plate 210. In such embodiments, the second drainage tube 230 may not be present.

Figure 4A:
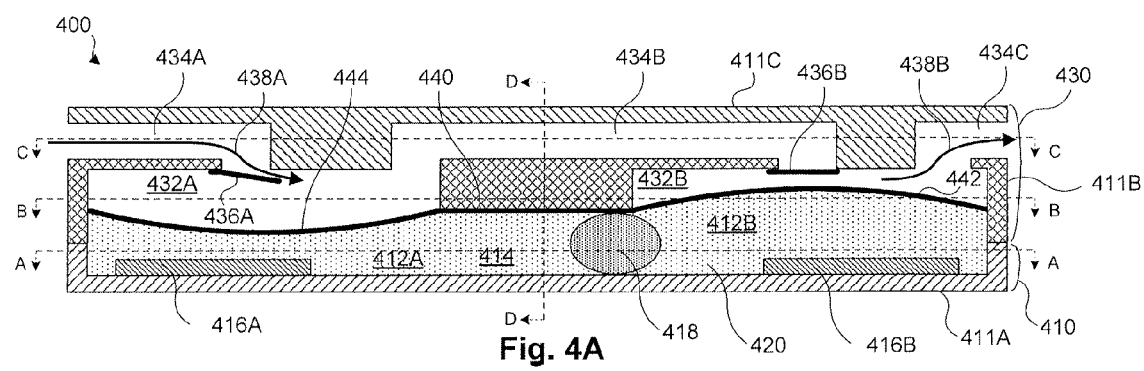
FIG. 4A is a cross-sectional view of a microfluidic pump in a first activated state such as may be used in the intraocular implant according to exemplary aspects of the present disclosure.

FIG. 4A is a cross-sectional view of a microfluidic pump 400 in a first activated state. The microfluidic pump 400 includes an actuating portion 410 and an actuated portion 430. In some embodiments, the actuating portion 410 is provided by a first substrate 411A, or in other embodiments by a first portion of a substrate. The actuating portion 410 and the actuated portion 430 may be made from glass, silicon, silicone, or a biocompatible polymer such as Parylene or polyimide, and may be milled, molded, or etched to provide their desired forms. As illustrated, the actuated portion 430 is formed from two substrates coupled together, substrate 411B and 411C. The substrate 411A-C may be shaped prior to being adhesively joined or bonded together. FIG. 4 illustrates a flexible membrane 440 disposed in between the actuating portion 410 and the actuated portion 430. In some embodiments, multiple flexible membranes are provided such that each covers limited portions of the actuating portion 410 and the actuated portion 430.

The actuating portion 410 includes a first chamber 412A coupled to a second chamber 412B by a narrow channel 414. The narrow channel is formed by the actuating portion 410 on the bottom and by the actuated portion 430 on top. The chambers 412A and 412B are defined by the internal walls of the substrate 411A that forms the actuating portion 410 on the sides and on the bottom and by the flexible membrane 440 on top. As used herein, terms such as "bottom", "top", and "sides", are used to describe relationships between features and are used with reference to the particular orientation of aspects as illustrated in the figures; the terms do not prescribe any particular orientation. For example, in some embodiments of the pump actuator 400, the actuating portion 410 is above the actuated portion 430.

Within each of the chambers 412A and 412B is an electrode 416A and 416B, respectively. The electrodes 416A and 416B may be formed from platinum, gold, or another conductive material. The conductive material of the electrodes 416A and 416B may be a biocompatible conductive material. Within the channel 414 is a conductive, immiscible slug 418. The slug 418 is surrounded by an electrolytic solution 420, such as a salt solution, that fills the chambers 412A and 412B and the remainder of the channel 414. In the illustrated embodiment, the slug 418 is formed from gallium. In other embodiments, the slug 418 may be formed from mercury or another conductor that is liquid at the temperature of the human body. When the actuator 400 is not activated, the slug 418 is positioned within the center of channel 414, such that it is halfway between the electrodes 416A and 416B and the membrane 440 is substantially undeflected. When activated by an electric potential applied to the electrodes 416A and 416B, a gradient is formed in the surface tension along the slug 418 immersed in the electrolytic solution 420. The gradient in surface tension produces a force that causes the slug 418 to move within the channel 414 toward either the electrode 416A or the electrode 416B depending on whether the electric potential is positive or negative. The gradient in surface tension γ is related to the electrical potential U by equation (1).

$$\gamma = \gamma_0 - \frac{1}{2}C(U - U_0) \quad (1)$$

In equation (1), C is the capacitance per unit area of the electrical double layer than forms between the slug 418 and the electrolytic solution 420.

As illustrated in FIG. 4A, the slug 418 is at an extreme end of the channel 414, closest to the chamber 412B, due to an applied electric potential. As the slug 418 moves toward the chamber 412B the slug increases the pressure within the chamber 412B, which results in the deflection 442 of the membrane 440 away from the chamber 412B. The deflection 442 effectively expands the volume of the chamber 412B. A corresponding deflection 444 occurs in the portion of the membrane 440 that partially defines the chamber 412A. The deflection 444 is toward the chamber 412A, such that the volume thereof is decreased. As the volume of the chamber 412A decreases, a corresponding reservoir 432A, located above the chamber 412A expands. Similarly, as the volume of the chamber 412B increases as the slug 418 moves toward it, the volume of a reservoir 432B located thereover increases. The changes in volume of the reservoirs 432A and 432B cause a fluid within a flow path of the pump 400 to flow through the pump 400.

The flow path of the microfluidic pump 400 includes several channels that permit fluid to enter and exit the microfluidic pump 400. As illustrated, the flow path includes a pump inlet channel 434A. The pump inlet channel 434A may be coupled to the drainage tube 220 of FIGS. 2 and 3, and thus, may allow aqueous humor to be drained from the anterior chamber 180 of the eye 100 by pumping the aqueous humor out. A pump channel 434B couples an outlet of the reservoir 432A to an inlet of the reservoir 432B, and an outlet pump channel 434C couples an outlet of the reservoir 432B to a drainage site. A tube, such as the drainage tube 230 of FIGS. 2 and 3, may be used to couple the pump outlet channel 434C to a drainage site, such as under the bleb 304. Thus, the flow path of the microfluidic pump 400 includes the pump inlet channel 434A, the pump channel 434B, and the pump outlet channel 434C. In the flow path of the pump 400 there are several valves that prevent backflow of aqueous humor into the eye 100. A first valve 436A is situated within the reservoir 432A. When the deflection 444 is toward the chamber 412A, and the reservoir 432A expands, a pressure difference across valve 436A is formed such that the valve 436A opens and fluid flows through the pump inlet channel 436A into the reservoir 432A, as indicated by the flow arrow 438A.

If the electric potential is removed, the differences in pressure between the chambers 412A and 412B naturally adjust, forcing the slug 418 back into the middle of the channel 414 and leveling the portions of the membrane 440 in the chambers 412A and 412B.

Figure 4B:
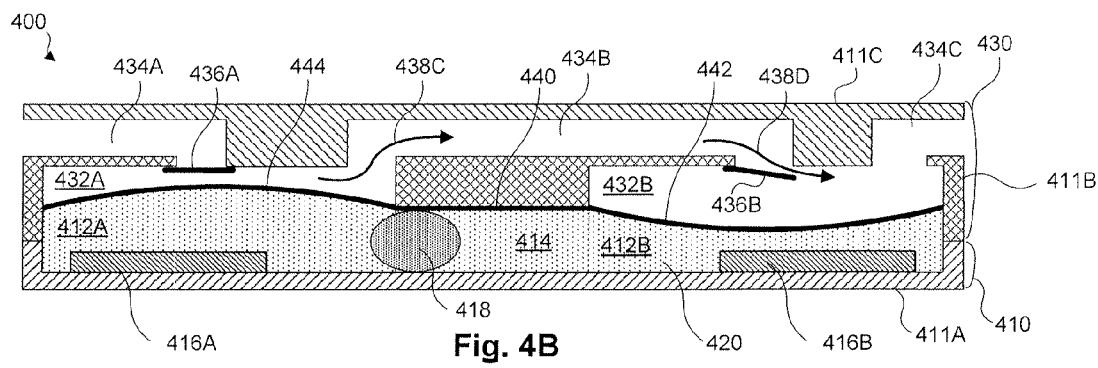
FIG. 4B is a cross-sectional view of the microfluidic pump of FIG. 4A in a second activated state according to exemplary aspects of the present disclosure.

As seen in FIG. 4B, a negative electric potential is applied to the electrodes 416A and 416B, which causes the slug 418 to move to the other extreme of the channel 414. The movement of the slug 418 causes the portion of membrane 440 over the chamber 412A to deflect away from the chamber 412A and the portion of the membrane 440 over the chamber 412B to deflect into the chamber 412B. This causes the volume of the reservoir 432A to decrease and the volume of the reservoir 432B to increase. The decrease in volume of the reservoir 432A is accompanied by an increase in pressure that closes the valve 436A, preventing backflow of fluid out of the pump inlet channel 434A. Instead, the fluid is forced through the pump channel 434B opening the valve 436B so that the fluid can enter the reservoir 436B. This flow is indicated by the flow arrows 438C and 438D.

As an electric potential is applied and then removed and a negative electric potential is applied and then removed in a continued cycle, aqueous humor is pumped by the pump 400 from the anterior chamber to a drainage site. The cycling may be performed at a frequency ranging from 0.1 hertz to about 100 hertz. The pump 400 may allow the draining to occur even when resistance is applied at the drainage site, such as by complications with the bleb 304.

Figure 5A:
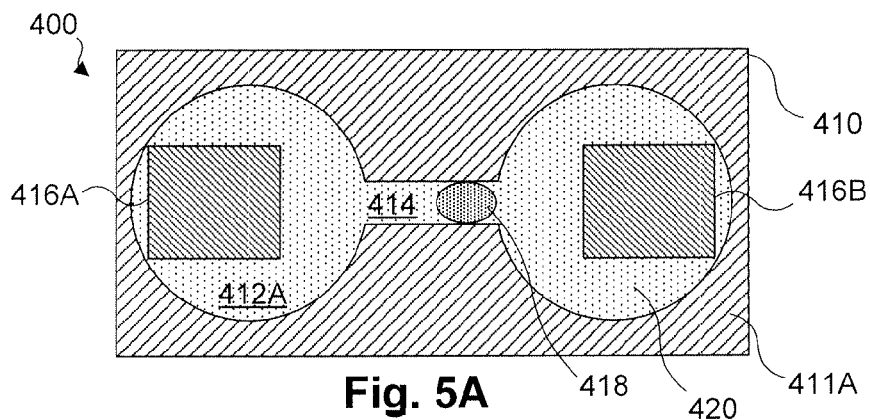
FIGS. 5A, 5B, 5C, and 5D are cross-sectional views of the entire microfluidic pump of FIGS. 4A and 4B as seen according to lines presented in FIG. 4A according to exemplary aspects of the present disclosure.

Referring now to FIGS. 5A, 5B, 5C, and 5D, FIGS. 5A-D present additional cross-sectional views of the pump 400 as described herein and illustrated in FIG. 4A. FIG. 5A is a view looking down at a cross-section according to line A-A of FIG. 4A. FIG. 5A depicts the actuated portion 410, including the chambers 412A and 412B. As illustrated, the chambers 412A and 412B are circular in shape. While other embodiments may include chambers of other shapes such as ovoid or rectangular, the circular chambers 412A and 412B in FIG. 5A may permit the portions of the membrane 440 to flex uniformly. The electrodes 416A and 416B are positioned within the chambers 412A and 412B. While depicted as rectangular, the electrodes 416A and 416B may be formed in other shapes in other embodiments.

Figure 5B:
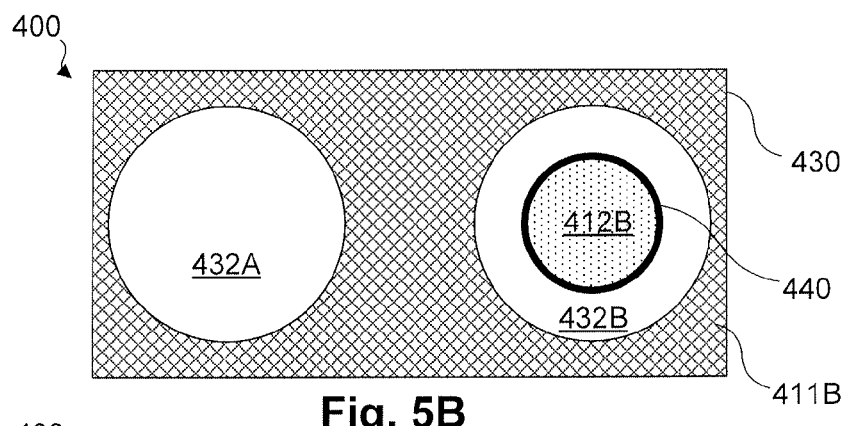
Figure 5C:
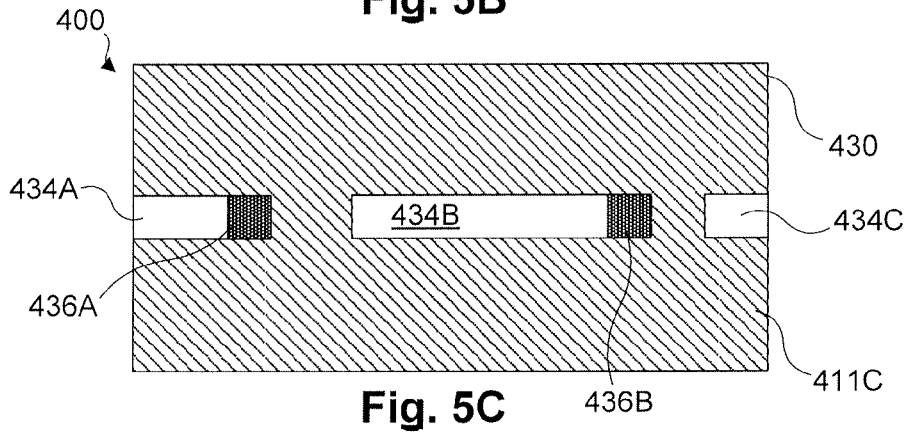

FIG. 5B is a cross-sectional view of the pump 400 as taken along line B-B of FIG. 4A. FIG. 5B shows part of the actuated portion 430 of the pump 400. The reservoir 432A and part of the reservoir 432B are depicted in FIG. 5B. Due to the deflection 442, part of the membrane 440 over the chamber 412B is shown, as is part of the chamber 412B itself. The flow path of the pump 400 described herein is shown in FIG. 5C. FIG. 5C is a view looking down on a cross-section of the pump 400 taken along the line C-C of FIG. 4A. FIG. 5C illustrates another cross-section of the actuated portion 430, as provided by the substrate 411C. FIG. 5C illustrates the flow path of the pump 400, which includes the pump inlet channel 434A, the pump channel 434B, and the pump outlet channel 434C. Also illustrated therein as the valves 436A and 436B that prevent backflow in the flow path of the pump 400. Other features, such as additional channels may be present in the actuated portion 430 that are not pertinent to the present disclosure and so are not illustrated in FIG. 5C.

Figure 5D:
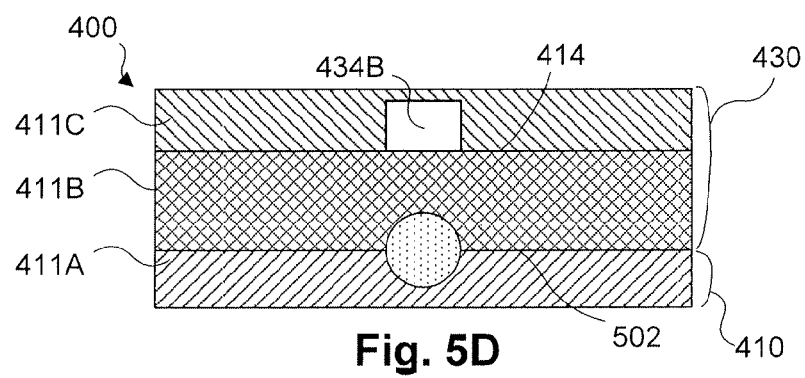

Referring now to FIG. 5D, a cross-section of the microfluidic pump 400 is illustrated therein. The cross-section of FIG. 5D is as seen according to the line D-D in FIG. 4A. The cross-section of FIG. 5D illustrates the substrate 411A that provides the actuating portion 410 in the depicted embodiment and also illustrates the substrates 411B and 411C that provide the actuated portion 430. As seen in FIG. 5D, the channel 414 is a generally circular channel, with half of the channel 414 provided by the actuating portion 410 and the other half being provided by a protrusion 502 of the actuated portion 430. The circular cross-section of the channel 414 may provide an optimal seal between the slug 418 and the walls of the channel 414, such that electrolytic solution 420 does not move easily from one side of the slug 418 to the other and from one of chambers 412A and 412B to the other.

Figure 6A:
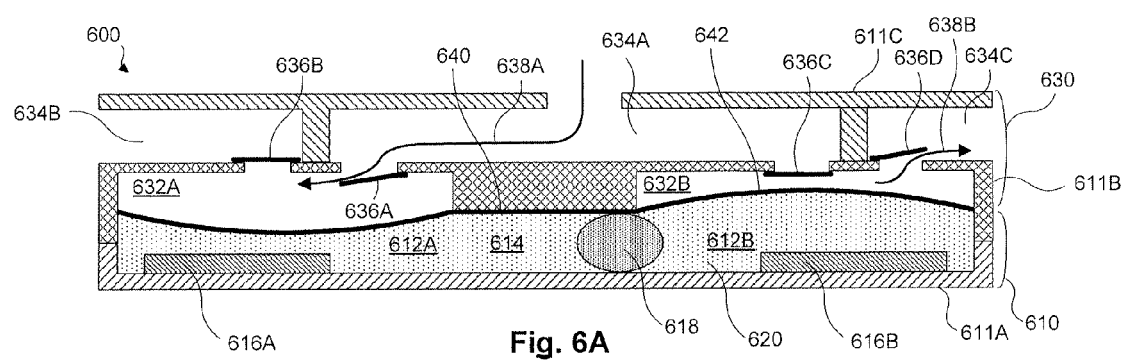
FIG. 6A is a cross-sectional view of another microfluidic pump in a first activated state such as may be used in the intraocular implant according to exemplary aspects of the present disclosure.
Figure 6B:
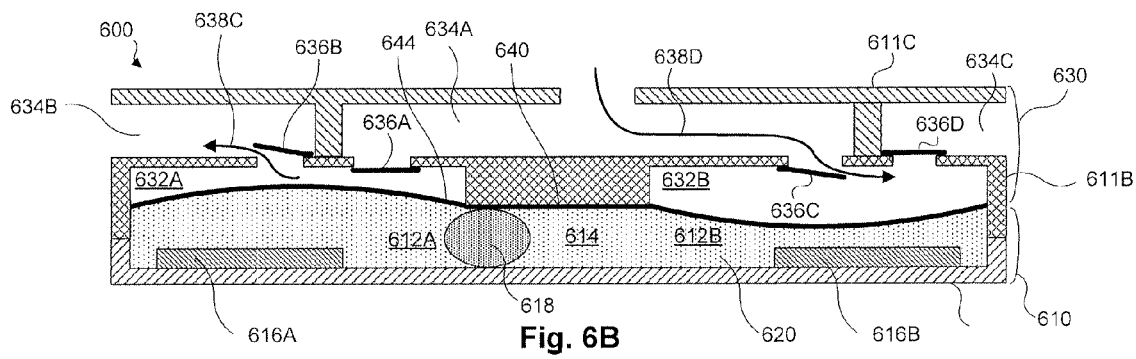
FIG. 6B is a cross-sectional view of the microfluidic pump of FIG. 6A in a second activated state according to exemplary aspects of the present disclosure.

FIGS. 6A and 6B are cross-sectional views of a microfluidic pump 600 that may be used in some embodiments of the intraocular device 200 as seen in FIGS. 2 and 3 to effectively drain aqueous humor from the anterior chamber of a patient's eye. The microfluidic pump 400 and the microfluidic pump 600 share several features in common. Thus, the microfluidic pump 600 includes an actuating portion 610 and an actuated portion 630. In the illustrated embodiments of FIGS. 6A and 6B, the actuating portion 610 is provided by a first substrate 511A, while the actuated portion 630 is provided by a second substrate 511B and a third substrate 511C. Other embodiments may be formed from fewer, or from more, substrates.

The actuating portion 610 include a microfluidic actuator that includes a first chamber 612A coupled to a second chamber 612B by a channel 614. Each of the chambers 612A and 612B includes an electrode 616A and 616B, respectively. The electrodes are configured to controllably move an immiscible slug 618, which is surrounded by an electrolytic fluid 620 that fills the chambers 612A and 612B and the channel 614. A membrane 640 is illustrated between the actuating portion 610 and the actuated portion 630. As the slug 618 is moved by application of an electric potential to the electrolytic fluid 620, which generates a surface tension gradient along the slug 618 immersed in the electrolytic fluid 620, the portions of the membrane 640 over the chambers 612A and 612B deflect away from a level, resting position. The gradient in surface tension γ is related to the electrical potential U by equation (1) as described herein. As seen in FIG. 6A, an electric potential is applied to the electrodes 616A and 616B such that the slug 618 is forced toward the chamber 612B, causing the deflection 642 of the membrane 640 into a reservoir 632B situated above and aligned with the chamber 612B. As the slug 618 moves toward the chamber 612B, the pressure within the chamber 612B increases, deflecting the membrane into the reservoir 632B, decreasing the volume thereof.

FIG. 6B illustrates the application of a negative electric potential (relative to the electric potential applied in FIG. 6A, which may be a positive or negative electric potential) to the electrodes 616A and 616B. The negative electric potential alters the surface tension gradient along the slug 618 immersed in the electrolytic fluid 620, forcing the slug 618 toward the electrode 616A. As the slug 618 moves, it pushes fluid in the channel 614 into the chamber 612A, increasing the pressure and causing the deflection 644 of the membrane 640 into a reservoir 632A. This decreases a volume of the reservoir 632A.

As an alternative electric potential is applied to the electrodes 616A and 616B of the actuating portion 610, the slug 618 oscillates within the channel 614 toward the chamber 612A and then to the chamber 612B. The alternating electric potential may oscillate at a frequency of around 1 hertz, although the frequency may range from about 0.1 hertz to about 100 hertz or more.

The pump 600 includes a flow path that includes several channels running through the actuated portion 630. In the illustrated embodiment, the flow path is formed in the substrate 611C. The flow path of the pump 600 is a branched flow path. As illustrated in FIGS. 6A and 6B, the flow path includes a pump inlet channel 634A, which may be coupled to the drainage tube 220 as seen in FIGS. 2 and 3 to permit fluid to enter the pump 600. As the pressure decreases within the chamber 623A, a valve 636A opens, thereby permitting fluid to enter from the pump inlet channel 634A. This flow is indicated by the flow arrow 638A. The valve 636A prevents fluid, such as aqueous humor from the eye of a patient from flowing back into the pump inlet channel 634A from the reservoir 632A. The pressure within the reservoir 632A is less than a pressure present in a first pump outlet channel 634B. This prevents fluid that has been pumped through the pump 600 from returning into the reservoir 432A by closing a valve 636B.

In the reservoir 632B, the pressure is higher than at the pump inlet channel 634A, and so a valve 636C, which couples the reservoir 632B to the pump inlet channel 634A, is forced closed. However, the pressure is also higher than a pressure within a second pump outlet channel 636B. This pressure difference opens a valve 636D that connects the reservoir 632B to the pump outlet channel 636B. This flow of liquid along the flow path is illustrated as a flow arrow 638B.

FIG. 6B shows the slug 618 as forced toward the electrode 616A in the chamber 612A. This increases the pressure within the chamber 612A, resulting in the deflection 644 of the membrane 640. The movement of the slug 618 also decreases the pressure within the chamber 612B. When the pressure within the reservoir 632A increases, the valve 636A closes, preventing back flow into the pump inlet channel 634A, and the valve 636B opens allowing fluid to exit the pump 600 through the first pump outlet channel 633B. This exiting fluid is depicted by the flow arrow 638C. The second reservoir 632B experiences a drop in pressure, which closes the valve 636D and opens the valve 636C, pulling fluid therethrough as illustrated by the flow arrow 638D.

Thus, during a first stroke, aqueous humor from the eye of a patient may be pumped out the pump outlet channel 634C. And during a second stroke, aqueous humor is pumped out of the pump outlet channel 634B. Thus, the flow path, which includes the pump inlet channel 634A and the pump outlet channels 634B and 634C, includes branched flow path, such that aqueous humor enters the pump through a single inlet, but may leave the pump through more than one outlet. The pump outlet channels 634B and 634C may be coupled to different drainage tubes in some embodiments. In such embodiments, the intraocular device 200, in which the pump 600 is installed, may include additional drainage tubes. In some other embodiments, both the pump outlet channels 634B and 634C may be coupled to a single drainage tube, such as the drainage tube 230 of FIGS. 2 and 3.

The systems and methods disclosed herein may be used to provide better performance for intraocular devices, such as increased control over drainage from the anterior chamber to regulate the IOP. This may be done by using microfluidic actuators in a microfluidic pump as described. This may result in more effective treatment and more accurate data, thereby improving the overall clinical result.

Persons of ordinary skill in the art will appreciate that the embodiments encompassed by the present disclosure are not limited to the particular exemplary embodiments described above. In that regard, although illustrative embodiments have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A microfluidic pump for implantation proximate an eye of a patient, the microfluidic pump comprising:
   a first substrate that includes a microfluidic actuator, the microfluidic actuator comprising:
      a first chamber and a second chamber coupled by a channel;
      an electrode in each of the first and second chambers; and
      a slug positioned within the channel, the slug being displaceable by applying an electric potential to an electrolytic fluid in the first and second chambers and the channel;
   a first reservoir aligned with the first chamber;
   a first membrane portion separating the first reservoir and the first chamber;
   a second reservoir aligned with the second chamber;
   a second membrane portion separating the second reservoir and the second chamber, wherein each of the first and second reservoirs has an inlet and an outlet, each of the inlets having a valve that prevents backflow through the inlet, each of the outlets having a valve that prevents backflow through the outlet;
   a second substrate that comprises a pump inlet channel coupling the outlet of the first reservoir to the inlet of the second reservoir, a first pump outlet channel coupled to the inlet of the first reservoir, and a second pump outlet channel coupled to the outlet of the second reservoir, wherein the first and second substrates are coupled together, and further wherein the pump inlet channel, the first pump outlet channel, and the second pump outlet channel are located above the first and second reservoirs; and
   a third substrate, the first and second substrates being coupled by the third substrate, and wherein the third substrate supports the valves.

2. The microfluidic pump of claim 1, wherein the slug is made from a conductive biocompatible material that is liquid at body temperature.

3. The microfluidic pump of claim 1, wherein the flow path coupling the outlet of the first reservoir to the inlet of the second reservoir is formed on one side of the second substrate.

4. The microfluidic pump of claim 3, wherein the flow path is etched, milled, or molded into the second substrate.

5. The microfluidic pump of claim 1, wherein the first and second chambers and the first and second reservoirs are circular.

6. The microfluidic pump of claim 1, wherein when an electric potential is applied to the electrodes, the slug moves to an extreme end of the channel.

7. The microfluidic pump of claim 6, wherein when an opposite electric potential is applied to the electrodes the slug moves to another extreme end of the channel.

8. A microfluidic pump for implantation proximate an eye of a patient, the microfluidic pump comprising:
- a microfluidic actuator, the microfluidic actuator comprising:
- a first chamber; and
- a second chamber, the first and second chambers being coupled by a channel;
- a slug positioned within the channel, the slug being displaceable by applying an electric potential to an electrolytic fluid in the first and second chambers and the channel;
- a first reservoir aligned with the first chamber of the microfluidic actuator;
- a first membrane portion separating the first reservoir from the first chamber; wherein the microfluidic actuator is configured to deflect the first membrane portion into and out of the first reservoir,
- a second reservoir aligned with the second chamber of the microfluidic actuator;
- a second membrane portion separating the second reservoir from the second chamber, wherein the microfluidic actuator is configured to deflect the second membrane portion into and out of the second reservoir; and
- a first substrate having a flow path therethrough, wherein the flow path comprises an inlet channel coupling a pump inlet to an inlet of the first reservoir and to an inlet of the second reservoir, a first pump outlet channel coupled to the outlet of the first reservoir, and a second pump outlet channel coupled to the outlet of the second reservoir, wherein the substrate is coupled to the microfluidic actuator and the first and second reservoirs, and further wherein the pump inlet, the first pump outlet channel, and the second pump outlet channel are located above the first and second reservoirs.

9. The microfluidic pump of claim 8, wherein the flow path further comprises a first reservoir outlet and a second reservoir outlet.

10. The microfluidic pump of claim 9, wherein the inlet of the first reservoir, the inlet of the second reservoir, the first reservoir outlet, and the second reservoir outlet each have a valve to prevent backflow therethrough.

11. The microfluidic pump of claim 8, wherein the microfluidic actuator is formed in a second substrate and the first and second reservoirs are formed in a third substrate, the second and third substrates being coupled to the first substrate.

12. A intraocular device for implantation proximate an eye of a patient, the intraocular device comprising:
- a plate sized for positioning proximate the eye;
- a first drainage tube having a proximal end and a distal end, the distal end configured for insertion into the eye;
- a microfluidic pump disposed within the plate and coupled to the proximal end of the first drainage tube, the microfluidic pump comprising:
- a microfluidic actuator, the microfluidic actuator comprising:
- a first chamber; and
- a second chamber, the first and second chambers being coupled by a channel;
- a channel between the first and second chamber with a slug therein;
- an electrode in each of the first and second chambers to displace the slug positioned within the channel by application of an electric potential to an electrolytic fluid in the first and second chambers and the channel;
- a first reservoir aligned with the first chamber of the microfluidic actuator;
- a first membrane portion separating the first reservoir from the first chamber; wherein the microfluidic actuator is configured to deflect the first membrane portion into and out of the first reservoir,
- a second reservoir aligned with the second chamber of the microfluidic actuator;
- a second membrane portion separating the second reservoir from the second chamber, wherein the microfluidic actuator is configured to deflect the second membrane portion into and out of the second reservoir; and
- a first substrate having a flow path therethrough, wherein the flow path comprises an inlet channel coupling a pump inlet to an inlet of the first reservoir and to an inlet of the second reservoir, a first pump outlet channel coupled to the outlet of the first reservoir, and a second pump outlet channel coupled to the outlet of the second reservoir, wherein the first substrate is coupled to the microfluidic actuator and the first and second reservoirs, and further wherein the pump inlet, the first pump outlet channel, and the second pump outlet channel are located above the first and second reservoirs.

13. The intraocular device of claim 12, wherein the microfluidic actuator is provided in a second substrate and the first and second reservoirs are provided in a third substrate, and the first, second, and third substrates are coupled together.

14. The intraocular device of claim 12, wherein the flow path comprises a first channel that couples an outlet of the first reservoir to an inlet of the second reservoir.

15. The intraocular device of claim 12, wherein the flow path comprises an inlet channel in communication with an inlet of the first reservoir and an inlet of the second reservoir, the first and second reservoirs each comprising an outlet.

16. The intraocular device of claim 15, wherein the first reservoir comprises a first valve that prevents backflow from the first reservoir into the inlet channel and the second reservoir comprises a second valve that prevents backflow from the second reservoir into the inlet channel.

17. The intraocular device of claim 12, wherein the first reservoir comprises an outlet valve that prevents backflow from an outlet channel into the first reservoir.

18. The intraocular device of claim 12, wherein the flow path comprises a first outlet channel coupled to the first reservoir and a second outlet channel coupled to the second reservoir.

* * * * *